United States Patent
Awasthi et al.

(10) Patent No.: US 11,660,370 B2
(45) Date of Patent: May 30, 2023

(54) OPHTHALMIC DEVICE PACKAGING SOLUTIONS COMPRISING TRIS(HYDROXYMETHYL)AMINOMETHANE AND NONIONIC SURFACTANT

(71) Applicant: Bausch & Lomb Incorporated, Rochester, NY (US)

(72) Inventors: Alok Kumar Awasthi, Pittsford, NY (US); Erning Xia, Penfield, NY (US); Jennah L. Wolcott, Perry, NY (US); Ruth Julian, Rochester, NY (US)

(73) Assignee: BAUSCH & LOMB INCORPORATED, Rochester, NY (US)

( * ) Notice: Subject to any disclaimer, the term of this patent is extended or adjusted under 35 U.S.C. 154(b) by 0 days.

(21) Appl. No.: 17/550,220

(22) Filed: Dec. 14, 2021

(65) Prior Publication Data
US 2022/0105230 A1    Apr. 7, 2022

Related U.S. Application Data

(62) Division of application No. 16/418,325, filed on May 21, 2019, now Pat. No. 11,253,625.

(60) Provisional application No. 62/690,497, filed on Jun. 27, 2018.

(51) Int. Cl.
| | |
|---|---|
| *C11D 1/722* | (2006.01) |
| *A61L 12/08* | (2006.01) |
| *A61L 12/04* | (2006.01) |
| *A61L 12/12* | (2006.01) |
| *B65B 25/00* | (2006.01) |
| *C11D 3/00* | (2006.01) |

(52) U.S. Cl.
CPC ............ *A61L 12/086* (2013.01); *A61L 12/04* (2013.01); *A61L 12/12* (2013.01); *B65B 25/008* (2013.01); *C11D 3/0078* (2013.01)

(58) Field of Classification Search
CPC ......... C11D 1/722; C11D 3/0078; C11D 3/30; C11D 3/3723; C11D 7/50; C11D 7/5022; C11D 7/5081; C11D 3/361; C11D 3/2065
See application file for complete search history.

(56) References Cited

U.S. PATENT DOCUMENTS

| | | | |
|---|---|---|---|
| 5,817,277 A | 10/1998 | Mowrey-Mckee et al. | |
| 5,882,687 A | 3/1999 | Park et al. | |
| 6,037,328 A | 3/2000 | Hu et al. | |
| 6,517,933 B1 | 2/2003 | Soane et al. | |
| 7,578,996 B2 | 8/2009 | Yu et al. | |
| 7,942,929 B2* | 5/2011 | Linhardt | C08F 230/00 428/420 |
| 9,309,357 B2 | 4/2016 | Awasthi et al. | |
| 2002/0071789 A1 | 6/2002 | Molock et al. | |
| 2002/0115578 A1 | 8/2002 | Groemminger | |
| 2003/0044468 A1 | 3/2003 | Cellesi et al. | |
| 2005/0215516 A1 | 9/2005 | Bucolo et al. | |
| 2007/0149428 A1 | 6/2007 | Ammon et al. | |
| 2007/0195261 A1* | 8/2007 | Vogt | C11D 1/722 351/158 |
| 2008/0093247 A1* | 4/2008 | Han | A61K 47/26 206/438 |
| 2008/0152540 A1 | 6/2008 | Schorzman et al. | |
| 2010/0266713 A1 | 10/2010 | Kabra | |
| 2010/0286010 A1 | 11/2010 | Xie et al. | |
| 2012/0006695 A1* | 1/2012 | Kawai | B65B 25/008 351/159.02 |
| 2012/0194779 A1* | 8/2012 | Zhang | C08J 7/16 427/164 |
| 2013/0276407 A1 | 10/2013 | Zhao | |
| 2013/0293833 A1* | 11/2013 | Tanaka | G02C 7/024 351/159.36 |
| 2014/0174962 A1* | 6/2014 | Luk | G02B 1/043 53/425 |
| 2014/0179825 A1* | 6/2014 | Rogers | B65B 23/00 53/428 |
| 2015/0024987 A1* | 1/2015 | Matsuoka | C11D 3/3773 510/112 |
| 2019/0179055 A1 | 6/2019 | Qiu et al. | |
| 2019/0224120 A1* | 7/2019 | Horn | A61K 47/40 |
| 2019/0263971 A1 | 8/2019 | Zhang et al. | |

FOREIGN PATENT DOCUMENTS

| | | |
|---|---|---|
| CN | 1479633 A | 3/2004 |
| CN | 101400378 A | 4/2009 |
| CN | 101909477 A | 12/2010 |
| CN | 102271719 A | 12/2011 |
| CN | 102670641 A | 9/2012 |
| CN | 103719142 A | 4/2014 |
| CN | 201980041365.X | 3/2022 |
| CN | 201980041365.X | 7/2022 |
| WO | 2007070653 A2 | 6/2007 |
| WO | 2008/079522 A1 | 7/2008 |
| WO | 2011/037893 A2 | 3/2011 |
| WO | 2014096853 A1 | 6/2014 |
| WO | PCT/US2019033299 | 9/2019 |

OTHER PUBLICATIONS

N. Schuerer et al., "Implications for Ophthalmic Formulations: Ocular Buffers Show Varied Cytotoxic Impact on Human Corneal-Limbal and Human Conjunctival Epithelial Cells," Cornea: The Journal of Cornea and External Disease, Jul. 2017, pp. 712-718, vol. 36, No. 6.

(Continued)

Primary Examiner — Charles I Boyer
(74) Attorney, Agent, or Firm — Ryan, Mason & Lewis, LLP

(57) ABSTRACT

A packaging system for storing ophthalmic devices such as contact lenses and methods for packaging such ophthalmic devices with solutions is disclosed. The packaging system contains an unused, ophthalmic device in an aqueous packaging solution comprising tris(hydroxymethyl)aminomethane or a salt thereof; wherein the solution has an osmolality of at least about 200 mOsm/kg and a pH in the range of about 6 to about 9.

20 Claims, 1 Drawing Sheet

(56) References Cited

OTHER PUBLICATIONS

N. Schrage et al., "Changing the Composition of Buffered Eye Drops Prevents Undesired Side Effects," British Journal of Ophthalmology, Jul. 21, 2010, pp. 1519-1522, vol. 94, No. 11.

* cited by examiner

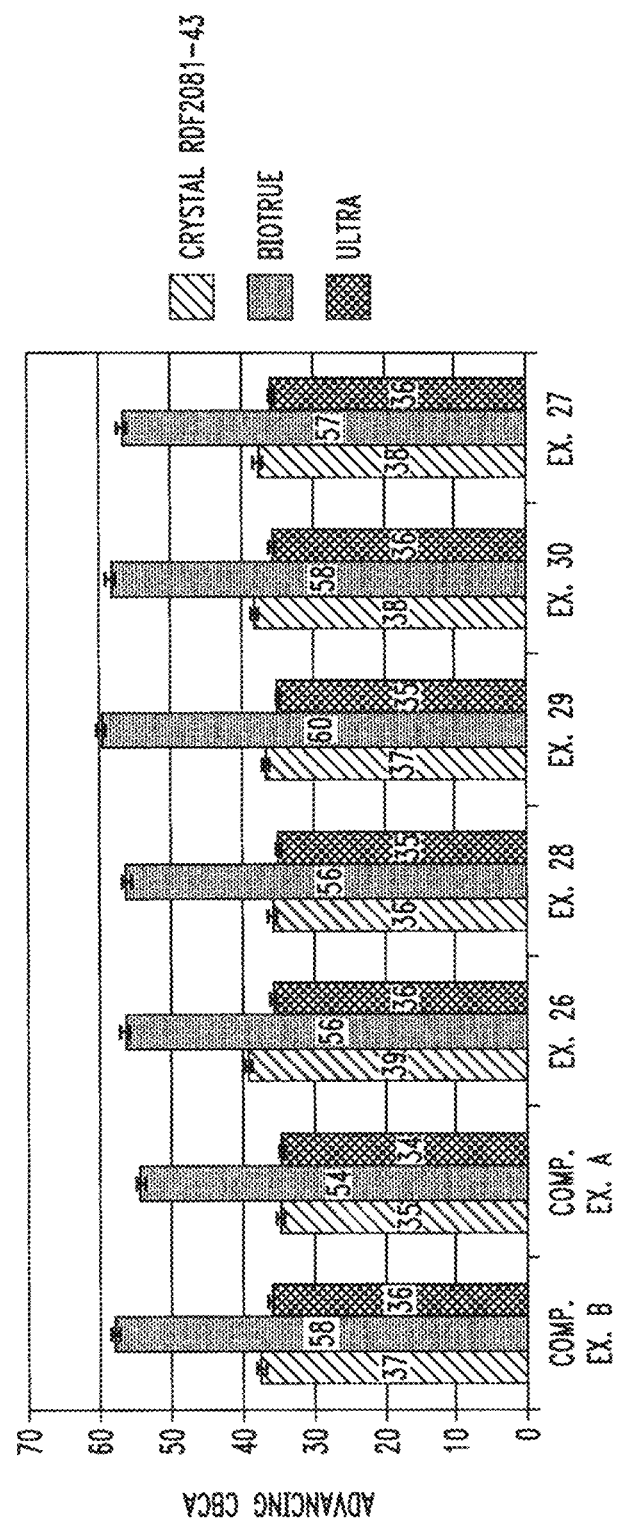

OPHTHALMIC DEVICE PACKAGING SOLUTIONS COMPRISING TRIS(HYDROXYMETHYL)AMINOMETHANE AND NONIONIC SURFACTANT

PRIORITY CLAIM

The present application is a divisional application of U.S. Ser. No. 16/418,325, filed May 21, 2019, now U.S. Pat. No. 11,253,625, which claims priority to U.S. Provisional Patent Application Ser. No. 62/690,497, entitled "Packaging Solutions," filed Jun. 27, 2018, the contents of each being incorporated by reference herein in their entirety.

BACKGROUND

The present invention generally relates to packaging solutions for ophthalmic devices such as contact lenses.

Blister-packs and glass vials are typically used to individually package each soft contact lens for sale to a customer. Saline or deionized water is commonly used to store the lens in the blister-packs, as mentioned in various patents related to the packaging or manufacturing of contact lenses. Because lens material may tend to stick to itself and to the lens package, packaging solutions for blister-packs have sometimes been formulated to reduce or eliminate lens folding and sticking.

It is highly desirable that contact lens be as comfortable as possible for wearers. Manufacturers of contact lenses are continually working to improve the comfort of the lenses. Nevertheless, many people who wear contact lenses still experience dryness or eye irritation throughout the day and particularly towards the end of the day. It has been stated that if a lens is thoroughly cleaned before insertion, lacrimal fluid can adequately wet the lens. However, an insufficiently wetted lens at any point in time will cause significant discomfort to the lens wearer. Although wetting drops can be used as needed to alleviate such discomfort, it would certainly be desirable if such discomfort did not arise in the first place.

It would be desirable to provide an improved packaging system for ophthalmic devices such as a contact lens such that the lens would be comfortable to wear in actual use and allow for extended wear of the lens without irritation or other adverse effects to the cornea.

SUMMARY

In accordance with one embodiment of the present invention, a packaging system for the storage of an ophthalmic device comprising a sealed container that contains an unused, ophthalmic device in an aqueous packaging solution comprising tris(hydroxymethyl)aminomethane or a salt thereof; wherein the solution has an osmolality of at least about 200 mOsm/kg and a pH in the range of about 6 to about 9.

In accordance with a second embodiment of the present invention, a method of preparing a package comprising a storable, sterile ophthalmic device is provided comprising:

(a) immersing an ophthalmic device in an aqueous packaging solution comprising tris(hydroxymethyl)aminomethane or a salt thereof; wherein the solution has an osmolality of at least about 200 mOsm/kg and a pH in the range of about 6 to about 9;

(b) packaging the solution and the ophthalmic device in a manner preventing contamination of the device by microorganisms; and (c) sterilizing the packaged solution and ophthalmic device.

The aqueous packaging solutions of the present invention containing at least tris(hydroxymethyl)aminomethane or a salt thereof result in a buffering system which provides a better stability profile and performance characteristics for actives such as hyaluronic acid as well as manufacturing advantages.

BRIEF DESCRIPTION OF THE DRAWING

FIG. 1 shows the bar graph of the CBCA for the packaged lenses of Examples 32-34.

DETAILED DESCRIPTION

The present invention provides a packaging system for the storage of ophthalmic devices intended for direct contact with body tissue or body fluid. As used herein, the term "ophthalmic device" refers to devices that reside in or on the eye. These lenses can provide optical correction, wound care, drug delivery, diagnostic functionality or cosmetic enhancement or effect or a combination of these properties. Representative examples of such devices include, but are not limited to, soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking. Any material known to produce an ophthalmic device including a contact lens can be used herein.

The ophthalmic device will be immersed in an aqueous packaging solution and stored in a packaging system according to the present invention. Generally, a packaging system for the storage of the ophthalmic device according to the present invention includes at least a sealed container containing one or more unused ophthalmic devices as described hereinabove immersed in an aqueous packaging solution. Preferably, the sealed container is a hermetically sealed blister-pack, in which a concave well containing the ophthalmic device is covered by a metal or plastic sheet adapted for peeling in order to open the blister-pack. The sealed container may be any suitable generally inert packaging material providing a reasonable degree of protection to the lens, preferably a plastic material such as polyalkylene, PVC, polyamide, and the like.

In general, the aqueous packaging solution will contain at least tris(hydroxymethyl)aminomethane (2-amino-2-(hydroxymethyl)propane-1,3-diol), (also known as tromethamine, and commonly referred to as tris, tris buffer, trizma or tris base) or a salt thereof. In one preferred embodiment, the first component is tris(hydroxymethyl)aminomethane in the HCl form.

In one embodiment, the tris(hydroxymethyl)aminomethane or a salt thereof is present in the aqueous packaging solution according to the present invention in an amount ranging from about 0.001 to about 1 wt. %, based on the total weight of the aqueous packaging solution. In another embodiment, the tris(hydroxymethyl)aminomethane or salt thereof is present in the aqueous packaging solution according to the present invention in an amount ranging from about 0.05 to about 1 wt. %, based on the total weight of the aqueous packaging solution.

In one embodiment, the packaging solution for use in the packaging system according to the present invention can further comprise one or more additional buffer agents. Suitable one or more additional buffer agents include, for example, phosphate buffer agents, borate buffer agents, citrate buffer agents, and the like. A suitable phosphate buffer agent can be any known phosphate buffer agents. In one embodiment, the phosphate buffer agent comprises one or more of sodium hydrogen phosphate monobasic, sodium hydrogen phosphate dibasic, potassium hydrogen phosphate monobasic and potassium hydrogen phosphate dibasic and any suitable hydrate thereof, e.g., monohydrate and heptahydrate. A suitable borate buffer agent can be any known borate buffer agents. In one embodiment, the borate buffer agent comprises one or more of boric acid and sodium borate. A suitable citrate buffer agent can be any known citrate buffer agents. In one embodiment, the citrate buffer agent comprises one or more of citric acid and sodium citrate.

In one embodiment, the one or more additional buffer agents are present in the packaging solution in an amount ranging from about 0.001 to about 2 wt. %, based on the total weight of the packaging solution. In one embodiment, the phosphate buffer agent is present in the packaging solution in an amount ranging from about 0.001 to about 2 wt. %, based on the total weight of the packaging solution.

In one embodiment, the packaging solution for use in the packaging system according to the present invention can further comprise one or more polysaccharides. In one embodiment, a polysaccharide comprises an anionic polysaccharide. Suitable anionic polysaccharides include, for example, hyaluronic acid or a salt thereof, e.g., sodium hyaluronate or potassium hyaluronate, chondroitin sulfate, chitosan, aloe vera, and carboxymethylcellulose. In one embodiment, a polysaccharide comprises a non-ionic polysaccharide. Suitable non-ionic polysaccharides include, for example, hemicellulose, hydroxypropyl methyl cellulose, methylcellulose, and ethylcellulose.

In one embodiment, the one or more polysaccharides are present in the packaging solution in an amount ranging from about 0.001 to about 10 wt. %, based on the total weight of the packaging solution.

In one embodiment, the packaging solution for use in the packaging system according to the present invention can further comprise one or more non-ionic surfactants. In one embodiment, one or more non-ionic surfactants can include, for example, one or more end terminal functionalized surfactants. A suitable end terminal functionalized surfactant includes, by way of example, one or more end terminal functionalized polyethers. Useful polyethers to be end terminal functionalized comprise one or more chains or polymeric components which have one or more (—O—R—) repeats units wherein R is an alkylene or arylene group having 2 to about 6 carbon atoms. The polyethers may be derived from block copolymers formed from different ratio components of ethylene oxide (EO) and propylene oxide (PO). Such polyethers and their respective component segments may include different attached hydrophobic and hydrophilic chemical functional group moieties and segments.

A representative example of a suitable polyether which can be end terminal functionalized is a poloxamer block copolymer. One specific class of poloxamer block copolymers are those available under the trademark Pluronic (BASF Wyandotte Corp., Wyandotte, Mich.). Poloxamers include Pluronics and reverse Pluronics. Pluronics are a series of ABA block copolymers composed of poly(ethylene oxide)-poly(propylene oxide)-poly(ethylene oxide) blocks as generally represented in Formula VII:

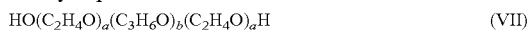

$$HO(C_2H_4O)_a(C_3H_6O)_b(C_2H_4O)_aH \qquad (VII)$$

wherein a is independently at least 1 and b is at least 1.

Reverse Pluronics are a series of BAB block copolymers, respectively composed of poly(propylene oxide)-poly(ethylene oxide)-poly(propylene oxide) blocks as generally represented in Formula VIII:

$$HO(C_3H_6O)_b(C_2H_4O)_a(C_3H_6O)_bH \qquad (VIII)$$

wherein a is at least 1 and b is independently at least 1. The poly(ethylene oxide), PEO, blocks are hydrophilic, whereas the poly(propylene oxide), PPO, blocks are hydrophobic in nature. The poloxamers in each series have varying ratios of PEO and PPO which ultimately determines the hydrophilic-lipophilic balance (HLB) of the material, i.e., the varying HLB values are based upon the varying values of a and b, a representing the number of hydrophilic poly(ethylene oxide) units (PEO) being present in the molecule and b representing the number of hydrophobic poly(propylene oxide) units (PPO) being present in the molecule.

Poloxamers and reverse poloxamers have terminal hydroxyl groups that can be terminal functionalized. An example of a terminal functionalized poloxamer and as discussed herein below is poloxamer dimethacrylate (e.g., Pluronic® F127 dimethacrylate) as disclosed in U.S. Patent Application Publication No. 2003/0044468 and U.S. Pat. No. 9,309,357. Other examples include glycidyl-terminated copolymers of polyethylene glycol and polypropylene glycol as disclosed in U.S. Pat. No. 6,517,933.

Another example of a suitable polyether which can be end terminal functionalized is a poloxamine block copolymer. While the poloxamers and reverse poloxamers are considered to be difunctional molecules (based on the terminal hydroxyl groups), the poloxamines are in a tetrafunctional form, i.e., the molecules are tetrafunctional block copolymers terminating in primary hydroxyl groups and linked by a central diamine. One specific class of poloxamine block copolymers are those available under the trademark Tetronic (BASF). Poloxamines include Tetronic and reverse Tetronics. Poloxamines have the following general structure of Formula IX:

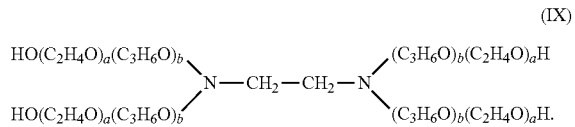

(IX)

wherein a is independently at least 1 and b is independently at least 1.

The poloxamer and/or poloxamine is functionalized to provide the desired reactivity at the end terminal of the molecule. The functionality can be varied and is determined based upon the intended use of the functionalized PEO- and PPO-containing block copolymers. That is, the PEO- and PPO-containing block copolymers are reacted to provide end terminal functionality that is complementary with the intended device forming monomeric mixture. The term block copolymer as used herein shall be understood to mean a poloxamer and/or poloxamine as having two or more blocks in their polymeric backbone(s).

In one embodiment, the one or more non-ionic surfactants are present in the packaging solution in an amount ranging from about 0.001 to about 10 wt. %, based on the total weight of the packaging solution.

In one embodiment, the packaging solution according to the present invention can further include one or more additives such as, for example, a poloxamer di(meth)acrylate, a reverse poloxamer di(meth)acrylate, a poloxamine di(meth)acrylate, a reverse poloxamine di(meth)acrylate, Mirj and Birj.

In one embodiment, the packaging solution according to the present invention can further include one or more additives such as, for example, trehalose L-Carnitine, erythritol, vitamin E TPGS (tocopheryl polyethylene glycol succinate), and the like.

In one embodiment, the packaging solution according to the present invention can further include one or more additives such as, for example, NaCl, KCl; amino taurine, glycine, diglycine, alanine; mannitol, sorbitol and propylene glycol.

The packaging solutions according to the present invention are physiologically compatible. Specifically, the solution must be "ophthalmically safe" for use with a lens such as a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe solution has a tonicity and pH that is compatible with the eye and includes materials, and amounts thereof, that are non-cytotoxic according to ISO standards and U.S. Food & Drug Administration (FDA) regulations.

The packaging solution should also be sterile in that the absence of microbial contaminants in the product prior to release must be statistically demonstrated to the degree necessary for such products. The liquid media useful in the present invention are selected to have no substantial detrimental effect on the lens being treated or cared for and to allow or even facilitate the present lens treatment or treatments. The liquid media are preferably aqueous-based. A particularly useful aqueous liquid medium is that derived from saline, for example, a conventional saline solution or a conventional buffered saline solution.

The pH of the present solutions is maintained within the range of about 6 to about 9, and preferably about 6.5 to about 7.8. As mentioned above, additional buffer may optionally be added, such as boric acid, sodium borate, potassium citrate, sodium citrate, citric acid, sodium bicarbonate, various mixed phosphate buffers (including combinations of $Na_2HPO_4$, $NaH_2PO_4$ and $KH_2PO_4$), hydrates thereof and the like and mixtures thereof. Generally, buffers will be used in amounts ranging from about 0.05 to about 2.5 percent by weight, and preferably from about 0.1 to about 1.5 percent by weight of the solution. However, according to certain embodiments, tris(hydroxymethyl)aminomethane, or salts thereof, function as the sole buffer.

Typically, the solutions of the present invention are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination, otherwise if simply blended with sterile water and made hypotonic or made hypertonic the lenses will lose their desirable optical parameters. Correspondingly, excess saline may result in the formation of a hypertonic solution which will cause stinging and eye irritation.

Examples of suitable tonicity adjusting agents include, but are not limited to, sodium and potassium chloride, dextrose, glycerin, calcium and magnesium chloride and the like and mixtures thereof. These agents are typically used individually in amounts ranging from about 0.01 to about 2.5% w/v and preferably from about 0.2 to about 1.5% w/v. Preferably, the tonicity agent will be employed in an amount to provide a final osmotic value of at least about 200 mOsm/kg, or from about 200 to about 400 mOsm/kg, or from about 250 to about 350 mOsm/kg, or from about 280 to about 320 mOsm/kg.

If desired, one or more additional components can be included in the packaging solution. Such additional component or components are chosen to impart or provide at least one beneficial or desired property to the packaging solution. Such additional components may be selected from components which are conventionally used in one or more ophthalmic device care compositions. Examples of such additional components include cleaning agents, wetting agents, nutrient agents, sequestering agents, viscosity builders, contact lens conditioning agents, antioxidants, and the like and mixtures thereof. These additional components may each be included in the packaging solutions in an amount effective to impart or provide the beneficial or desired property to the packaging solutions. For example, such additional components may be included in the packaging solutions in amounts similar to the amounts of such components used in other, e.g., conventional, contact lens care products.

Useful sequestering agents include, but are not limited to, disodium ethylene diamine tetraacetate, alkali metal hexametaphosphate, citric acid, sodium citrate and the like and mixtures thereof.

Useful viscosity builders include, but are not limited to, hydroxyethyl cellulose, hydroxymethyl cellulose, polyvinyl pyrrolidone, polyvinyl alcohol and the like and mixtures thereof.

Useful antioxidants include, but are not limited to, sodium metabisulfite, sodium thiosulfate, N-acetylcysteine, butylated hydroxyanisole, butylated hydroxytoluene and the like and mixtures thereof.

The method of packaging and storing an ophthalmic device such as a contact lens according to the present invention includes at least packaging an ophthalmic device immersed in the aqueous packaging solution described above. The method may include immersing the ophthalmic device in an aqueous packaging solution prior to delivery to the customer/wearer, directly following manufacture of the contact lens. Alternately, the packaging and storing in the solution of the present invention may occur at an intermediate point before delivery to the ultimate customer (wearer) but following manufacture and transportation of the lens in a dry state, wherein the dry lens is hydrated by immersing the lens in the packaging solution. Consequently, a package for delivery to a customer may include a sealed container containing one or more unused contact lenses immersed in an aqueous packaging solution according to the present invention.

In one embodiment, the steps leading to the present ophthalmic device packaging system includes (1) molding an ophthalmic device in a mold comprising at least a first and second mold portion, (2) hydrating and cleaning the device in a container comprising at least one of the mold portions, (3) introducing the packaging solution with the copolymer into the container with the device supported therein, and (4) sealing the container. Preferably, the method also includes the step of sterilizing the contents of the container. Sterilization may take place prior to, or most conveniently after, sealing of the container and may be effected by any suitable method known in the art, e.g., by autoclaving of the sealed container at temperatures of about 120° C. or higher.

The following examples are provided to enable one skilled in the art to practice the invention and are merely illustrative of the invention. The examples should not be read as limiting the scope of the invention as defined in the claims.

Various packaging solution were formed as discussed below and characterized by a standard testing procedure such as:

Contact Angle (CBCA): Captive bubble contact angle data was collected on a First Ten Angstroms FTA-1000 drop Shape Instrument. All samples were rinsed in HPLC grade water prior to analysis in order to remove components of the packaging solution from the sample surface. Prior to data collection the surface tension of the water used for all experiments was measured using the pendant drop method. In order for the water to qualify as appropriate for use, a surface tension value of 70-72 dynes/cm was expected. All lens samples were placed onto a curved sample holder and submerged into a quartz cell filled with HPLC grade water. Advancing and receding captive bubble contact angles were collected for each sample. The advancing contact angle is defined as the angle measured in water as the air bubble is retracting from the lens surface (water is advancing across the surface). All captive bubble data was collected using a high speed digital camera focused onto the sample/air bubble interface. The contact angle was calculated at the digital frame just prior to contact line movement across the sample/air bubble interface. The receding contact angle is defined as the angle measured in water as the air bubble is expanding across the sample surface (water is receding from the surface).

In the example, the following abbreviations are used.

CMC: Carboxymethyl cellulose polymer having a viscosity of 100 to 1000 cPs and represented by the structure:

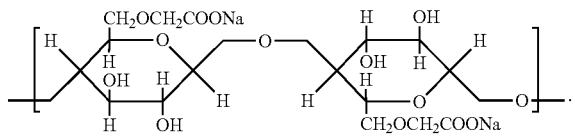

HPMC: Hydroxypropylmethyl cellulose polymer having a viscosity of about 2500 to about 5000 cPs and represented by the structure:

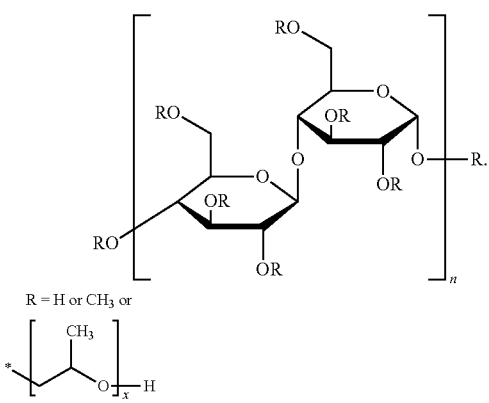

PDMA-C18-RAFT Surfactant: a poly(dimethylacrylamide) polymer having a number average molecular weight of about 10400 to about 65400, a weight average molecular weight of about 10700 to about 92050 Da and a polydispersity of about 1.03 to about 1.41, and is represented by the following structure:

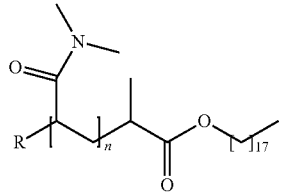

wherein R is CN, OH or H.

PVP-C18-RAFT Surfactant: a polyvinyl pyrrolidone polymer having a number average molecular weight of about 5600 to about 31300, a weight average molecular weight of about 6400 to about 41300 Da and a polydispersity of about 1.14 to about 1.32, and is represented by the following structure:

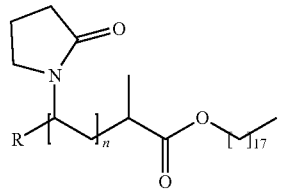

wherein R is CN, OH or H.

PDMA-VDO: a PolyDMA-co-vinyl-4,4-Dimethyl-2-oxazoline-5-one where m is 10 to 50 and n is 10 to 50 and having a number average molecular weight (Mn) from about 10,000 to about 50,000 and a weight average molecular weight (Mw) from about 15,000 to about 100,000 and a polydispersity of about 1.2 to about 2.0

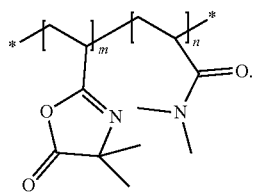

Poly(acrylic acid)-grafted-poly(ethylene glycol) (PAA-g-PEG): a grafted polymer wherein the number average molecular weight of the PAA backbone is 60 kDa, the number average molecular weight of the PEG side chains is 2 kDa and the PEG substitution is about 78%. The PAA-g-PEG grafted polymer is represented by the following structure:

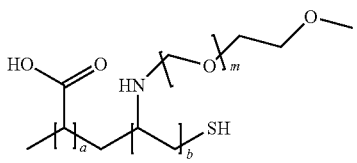

wherein m is 10 to 50, a is 10 to 50 and b is 10 to 50.

Poly(acrylic acid)-co-poly(ethylene glycol) monoether acrylate (PAA-co-PEG): a copolymer having the structure:

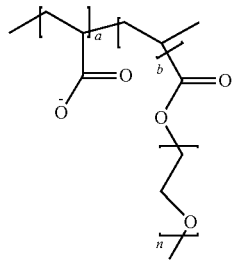

wherein n is 10-50, a is 10 to 50 and b is 10 to 50.

Poly(dimethylacrylamide)-co-poly(ethylene glycol methacrylate) (PDMA-co-PEGMA): a copolymer having a number average molecular weight of about 15 to about 80 kDa, a weight average molecular weight of about 19 to about 100 kDa and a polydispersity of about 1.30 to about 1.45. The PDMA-co-PEGMA copolymer is represented by the following structure:

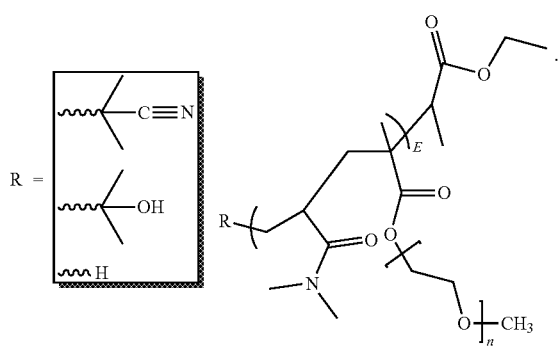

Poly(acrylic acid)-2-dimethyl ethylenediamine (PAA-2-dimethyl ethylenediamine): a polymer having the structure:

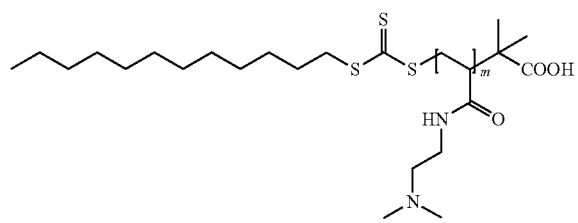

wherein m is 10 to 50.

Poly(acrylic acid)-ethylenediamine (boc deprotected) (PAA-ethylenediamine (boc deprotected): a deprotected polymer having the structure:

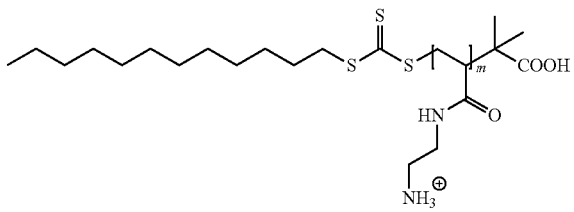

wherein m is 10 to 50.

Tetronic 1107: a block copolymer surfactant:

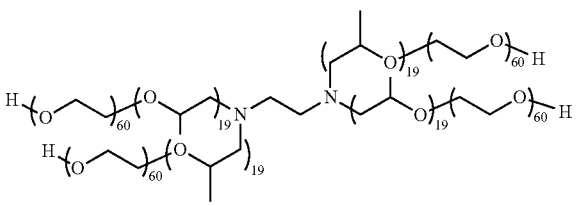

Example 1

A packaging solution is made by mixing the following components in the respective amounts listed in Table 1.

TABLE 1

| Ingredient | % W/V |
|---|---|
| Tris HCl | 0.530 |
| Trizma Base | 0.080 |
| Sodium Chloride | 0.720 |
| pH | 7.54 |
| Osmolality | 303 |

Example 2

A packaging solution is made by mixing the following components in the respective amounts listed in Table 2.

TABLE 2

| Ingredient | % W/V |
|---|---|
| Tris HCl | 0.530 |
| Trizma Base | 0.080 |
| Potassium Chloride | 0.780 |
| pH | 7.54 |
| Osmolality | 310 |

Example 3

A packaging solution is made by mixing the following components in the respective amounts listed in Table 3.

TABLE 3

| Ingredient | % W/V |
|---|---|
| Tris HCl | 0.530 |
| Trizma Base | 0.080 |
| Potassium Chloride | 0.780 |
| Tetronic 1107 | 0.50 |

TABLE 3-continued

| Ingredient | % W/V |
| --- | --- |
| pH | 7.54 |
| Osmolality | 310 |

Example 4

A packaging solution is made by mixing the following components in the respective amounts listed in Table 4.

TABLE 4

| Ingredient | % W/V |
| --- | --- |
| Tris HCl | 0.530 |
| Trizma Base | 0.080 |
| Potassium Chloride | 0.780 |
| Tetronic 1107 | 0.50 |
| Trehalose | 0.20 |
| pH | 7.40-7.60 |
| Osmolality | 320-370 |

Example 5

A packaging solution is made by mixing the following components in the respective amounts listed in Table 5.

TABLE 5

| Ingredient | % W/V |
| --- | --- |
| Tris HCl | 0.530 |
| Trizma Base | 0.080 |
| Potassium Chloride | 0.780 |
| Tetronic 1107 | 0.50 |
| Erythritol | 0.20-0.50 |
| pH | 7.40-7.60 |
| Osmolality | 320-370 |

Example 6

A packaging solution is made by mixing the following components in the respective amounts listed in Table 6.

TABLE 6

| Ingredient | % W/V |
| --- | --- |
| Tris HCl | 0.530 |
| Trizma Base | 0.080 |
| Potassium Chloride | 0.580 |
| Glycerin | 0.300 |
| Tetronic 1107 | 0.50 |
| Erythritol | 0.20-0.50 |
| pH | 7.40-7.60 |
| Osmolality | 320-370 |

Example 7

A packaging solution is made by mixing the following components in the respective amounts listed in Table 7.

TABLE 7

| Ingredient | % W/V |
| --- | --- |
| Tris HCl | 0.530 |
| Trizma Base | 0.080 |

TABLE 7-continued

| Ingredient | % W/V |
| --- | --- |
| Potassium Chloride | 0.580 |
| Propylene Glycol | 0.300 |
| Tetronic 1107 | 0.50 |
| Erythritol | 0.20-0.50 |
| pH | 7.40-7.60 |
| Osmolality | 320-370 |

Example 8

A packaging solution is made by mixing the following components in the respective amounts listed in Table 8.

TABLE 8

| Ingredient | % W/V |
| --- | --- |
| Tris HCl | 0.530 |
| Trizma Base | 0.080 |
| Potassium Chloride | 0.580 |
| Glycerin | 0.300 |
| Tetronic 1107 | 0.50 |
| L-Carnitine | 0.20-0.50 |
| pH | 7.40-7.60 |
| Osmolality | 320-370 |

Example 9

A packaging solution is made by mixing the following components in the respective amounts listed in Table 9.

TABLE 9

| Ingredient | % W/V |
| --- | --- |
| Tris HCl | 0.530 |
| Trizma Base | 0.080 |
| Potassium Chloride | 0.580 |
| Glycerin | 0.300 |
| Tetronic 1107 | 0.50 |
| L-Carnitine | 0.20-0.50 |
| Erythritol | 0.20-0.50 |
| pH | 7.40-7.60 |
| Osmolality | 320-370 |

Example 10

A packaging solution is made by mixing the following components in the respective amounts listed in Table 10.

TABLE 10

| Ingredient | % W/V |
| --- | --- |
| Tris HCl | 0.320 |
| Sodium Borate | 0.080 |
| Potassium Chloride | 0.580 |
| Glycerin | 0.300 |
| Tetronic 1107 | 0.50 |
| L-Carnitine | 0.20-0.50 |
| Erythritol | 0.20-0.50 |
| pH | 7.40-7.60 |
| Osmolality | 320-370 |

Example 11

A packaging solution is made by mixing the following components in the respective amounts listed in Table 11.

TABLE 11

| Ingredient | % W/V |
|---|---|
| Tris HCl | 0.320 |
| Sodium Phosphate, dibasic | 0.100 |
| Potassium Chloride | 0.580 |
| Glycerin | 0.300 |
| Tetronic 1107 | 0.50 |
| L-Carnitine | 0.20-0.50 |
| Erythritol | 0.20-0.50 |
| pH | 7.40-7.60 |
| Osmolality | 320-370 |

Example 12

A packaging solution is made by mixing the following components in the respective amounts listed in Table 12.

TABLE 12

| Ingredient | % W/V |
|---|---|
| Tris HCl | 0.530 |
| Trizma Base | 0.080 |
| Potassium Chloride | 0.580 |
| Glycerin | 0.300 |
| Tetronic 1107 | 0.50 |
| Hyaluronic acid | 0.05 |
| Erythritol | 0.20-0.50 |
| pH | 7.40-7.60 |
| Osmolality | 320-370 |

Example 13

A packaging solution is made by mixing the following components in the respective amounts listed in Table 13.

TABLE 13

| Ingredient | % W/V |
|---|---|
| Tris HCl | 0.320 |
| Sodium Citrate | 0.150 |
| Sodium Chloride | 0.580 |
| Glycerin | 0.300 |
| Tetronic 1107 | 0.50 |
| Hyaluronic acid | 0.05 |
| Erythritol | 0.20-0.50 |
| pH | 7.40-7.60 |
| Osmolality | 320-370 |

Example 14

A packaging solution is made by mixing the following components in the respective amounts listed in Table 14.

TABLE 14

| Ingredient | % W/W |
|---|---|
| Trizma HCl | 11.018 |
| Trizma Base | 2.045 |
| Sodium Chloride | 0.502 |
| Purified Water | 86.435 |
| Viscosity | 1.50-1.55 |
| pH | 7.45 |
| Osmolality | 1025 |

Example 15

A packaging solution is made by mixing the following components in the respective amounts listed in Table 15.

TABLE 15

| Ingredient | % W/W |
|---|---|
| Trizma HCl | 0.627 |
| Trizma Base | 0.116 |
| Sodium Chloride | 0.577 |
| Purified Water | 98.680 |
| Viscosity | 1.13-1.30 |
| pH | 7.55 |
| Osmolality | 272 |

Example 16

A packaging solution is made by mixing the following components in the respective amounts listed in Table 16.

TABLE 16

| Ingredient | % W/W |
|---|---|
| Trizma HCl | 0.627 |
| Trizma Base | 0.116 |
| Sodium Chloride | 0.577 |
| Purified Water | 98.680 |
| CMC | 0.05-0.25 |
| Viscosity | 1.42-3.37 |
| pH | 7.5-7.6 |
| Osmolality | 271-274 |

Example 17

A packaging solution is made by mixing the following components in the respective amounts listed in Table 17.

TABLE 17

| Ingredient | % W/W |
|---|---|
| Trizma HCl | 0.627 |
| Trizma Base | 0.116 |
| Sodium Chloride | 0.577 |
| Purified Water | 98.680 |
| PDMA-C18 | 0.05 |
| Viscosity | 1.20-1.34 |
| pH | 7.55 |
| Osmolality | 273 |

Example 18

A packaging solution is made by mixing the following components in the respective amounts listed in Table 18.

TABLE 18

| Ingredient | % W/W |
|---|---|
| Trizma HCl | 0.627 |
| Trizma Base | 0.116 |
| Sodium Chloride | 0.577 |
| Purified Water | 98.680 |
| PDMA-co-vinyl-4,4-dimethyl-2-oxazoline-5-one | 0.05 |
| Viscosity | 1.20-1.28 |

TABLE 18-continued

| Ingredient | % W/W |
|---|---|
| pH | 7.51 |
| Osmolality | 270 |

Example 19

A packaging solution is made by mixing the following components in the respective amounts listed in Table 19.

TABLE 19

| Ingredient | % W/W |
|---|---|
| Trizma HCl | 0.627 |
| Trizma Base | 0.116 |
| Sodium Chloride | 0.577 |
| Purified Water | 98.680 |
| PVP-C18 | 0.05 |
| Viscosity | 1.24-1.33 |
| pH | 7.53 |
| Osmolality | 269 |

Example 20

A packaging solution is made by mixing the following components in the respective amounts listed in Table 20.

TABLE 20

| Ingredient | % W/W |
|---|---|
| Trizma HCl | 0.627 |
| Trizma Base | 0.116 |
| Sodium Chloride | 0.577 |
| Purified Water | 98.680 |
| HPMC | 0.05-0.5 |
| Viscosity | 1.1-1.8 |
| pH | 7.1-7.8 |
| Osmolality | 200-400 |

Example 21

A packaging solution is made by mixing the following components in the respective amounts listed in Table 21.

TABLE 21

| Ingredient | % W/W |
|---|---|
| Trizma HCl | 0.627 |
| Trizma Base | 0.116 |
| Sodium Chloride | 0.577 |
| Purified Water | 98.680 |
| PAA-g-PEG | 0.02-0.5 |
| Viscosity | 1.1-1.8 |
| pH | 7.1-7.5 |
| Osmolality | 200-400 |

Example 22

A packaging solution is made by mixing the following components in the respective amounts listed in Table 22.

TABLE 22

| Ingredient | % W/W |
|---|---|
| Trizma HCl | 0.627 |
| Trizma Base | 0.116 |
| Sodium Chloride | 0.577 |
| Purified Water | 98.680 |
| PAA-co-PEG | 0.02-0.5 |
| Viscosity | 1.1-1.8 |
| pH | 7.1-7.5 |
| Osmolality | 200-400 |

Example 23

A packaging solution is made by mixing the following components in the respective amounts listed in Table 23.

TABLE 23

| Ingredient | % W/W |
|---|---|
| Trizma HCl | 0.627 |
| Trizma Base | 0.116 |
| Sodium Chloride | 0.577 |
| Purified Water | 98.680 |
| PDMA-co-PEG400MA | 0.02-0.5 |
| Viscosity | 1.1-1.8 |
| pH | 7.1-7.5 |
| Osmolality | 200-400 |

Example 24

A packaging solution is made by mixing the following components in the respective amounts listed in Table 24.

TABLE 24

| Ingredient | % W/W |
|---|---|
| Trizma HCl | 0.627 |
| Trizma Base | 0.116 |
| Sodium Chloride | 0.577 |
| Purified Water | 98.680 |
| PAA-amine | 0.02-0.5 |
| Viscosity | 1.1-1.8 |
| pH | 7.1-7.5 |
| Osmolality | 200-400 |

Example 25

A packaging solution is made by mixing the following components in the respective amounts listed in Table 25.

TABLE 25

| Ingredient | % W/W |
|---|---|
| Trizma HCl | 0.627 |
| Trizma Base | 0.116 |
| Sodium Chloride | 0.577 |
| Purified Water | 98.680 |
| Tetronic 1107 | 0.05-0.5 |
| Viscosity | 1.1-1.8 |
| pH | 7.1-7.5 |
| Osmolality | 200-400 |

Comparative Example A

A borated buffer packaging solution (BBS) was made by mixing the following components in the respective amounts listed in Table 26.

TABLE 26

| Ingredient | % W/W |
|---|---|
| Sodium Chloride | 0.459 |
| Sodium Borate | 0.125 |
| Boric Acid | 1.148 |
| Purified Water | 98.83 |
| Viscosity | 1.0-1.25 |
| pH | 7.1-7.4 |
| Osmolality | 330-350 |

Comparative Example B

A packaging solution was made by adding 0.5 wt. % Poloxamine 1107 to the BBS solution of Comparative Example A.

Example 26

A packaging solution was made by adding 0.25 wt. % CMC to the BBS solution of Comparative Example A.

Example 27

A packaging solution was made by adding 0.05 wt. % CMC to the BBS solution of Comparative Example A.

Example 28

A packaging solution was made by adding 0.05 wt. % PDMA-C18 to the BBS solution of Comparative Example A.

Example 29

A packaging solution was made by adding 0.05 wt. % PDMA-VDO to the BBS solution of Comparative Example A.

Example 30

A packaging solution was made by adding 0.05 wt. % PVP-C18 to the BBS solution of Comparative Example A.

Example 31

A nesofilcon A (BioTrue) lens was packaged in each of the packaging solutions of Comparative Examples A and B and Examples 26-30 and autoclaved for 30 min at 121° C.

Example 32

A samfilcon A (Ultra) lens was packaged in each of the packaging solutions of Comparative Examples A and B and Examples 26-30 and autoclaved for 30 min at 121° C.

Example 33

A new silicone daily disposable (Crystal RDF2081-43) lens was packaged in each of the packaging solutions of Comparative Examples A and B and Examples 26-30 and autoclaved for 30 min at 121° C.

Testing

Each of the packaged lenses of Examples 31-33 were removed from the package after and then measured for the lens diameters as set forth below in Tables 28-30.

TABLE 27

Crystal RDF2081-43 lens diameter data

| Solution | Diameter (mm) |
|---|---|
| Comp. Ex. A | 15.52 |
| Comp. Ex. B | 15.591 |
| Example 26 | 15.471 |
| Example 27 | 15.545 |
| Example 28 | 15.566 |
| Example 29 | 15.49 |
| Example 30 | 15.327 |

TABLE 28

BioTrue lens diameter data

| Solution | Diameter (mm) |
|---|---|
| Comp. Ex. A | 14.300 |
| Comp. Ex. B | 14.013 |
| Example 26 | 14.364 |
| Example 27 | 14.339 |
| Example 28 | 14.368 |
| Example 29 | 14.344 |
| Example 30 | 14.295 |

TABLE 29

Ultra lens diameter data

| Solution | Diameter (mm) |
|---|---|
| Comp. Ex. A | 14.327 |
| Comp. Ex. B | 14.238 |
| Example 26 | 14.620 |
| Example 27 | 14.221 |
| Example 28 | 14.383 |
| Example 29 | 14.530 |
| Example 30 | 14.366 |

Each of the packaged lenses of Examples 31-33 were removed from the packaging solution after and then measured for CBCA. The results of the data are set forth in FIG. 1.

Examples 34 and 35 and Comparative Example C

A packaging solution was made by mixing the following components in the respective amounts listed in Table 30.

TABLE 30

| Ingredients | EXAMPLE 34 | EXAMPLE 35 | Comp. Ex. C |
|---|---|---|---|
| Tris HCl, % wt/wt | 0.130 | 0.530 | — |
| Trizma base, % wt/wt | — | 0.075 | — |
| Sodium Phosphate Dibasic Heptahydrate, % wt/wt | 0.09 | — | — |
| Potassium Chloride, % wt/wt | 0.9 | 0.8 | — |
| Glycerin, % wt/wt | 0.73 | 0.55 | 0.55 |
| Erythritol, % wt/wt | 0.300 | 0.3 | 0.3 |
| Tetronic 1107, % wt/wt | 0.50 | 0.500 | 0.500 |
| Water | QS to 100% | QS to 100% | QS to 100% |
| pH | 7.40 | 7.55 | |
| Osmolality | 365 | 359 | |

Examples 36 and 37 and Comparative Example D

A packaging solution was made by mixing the following components in the respective amounts listed in Table 31.

TABLE 31

| Ingredients | EXAMPLE 36 | EXAMPLE 37 | Comp. Ex. D |
|---|---|---|---|
| Tris HCl, % wt/wt | 0.130 | 0.530 | — |
| Trizma base, % wt/wt | — | 0.075 | — |
| Sodium Phosphate Dibasic Heptahydrate, % wt/wt | 0.09 | — | — |
| Potassium Chloride, % wt/wt | 0.9 | 0.8 | — |
| Glycerin, % wt/wt | 0.73 | 0.55 | 0.55 |
| Erythritol, % wt/wt | 0.300 | 0.3 | 0.3 |
| Tetronic 1107, % wt/wt | 0.50 | 0.500 | 0.500 |
| Chondroitin Sulfate, % wt/wt | 0.50 | 0.50 | 0.50 |
| water | QS to 100% | QS to 100% | QS to 100% |
| pH | 7.40 | 7.55 | — |
| Osmolality | 365 | 359 | — |

It will be understood that various modifications may be made to the embodiments disclosed herein. Therefore, the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A method of preparing a package comprising a storable, sterile ophthalmic device, the method comprising:
   (a) immersing an ophthalmic device in an aqueous packaging solution comprising:
       (i) tris(hydroxymethyl)aminomethane or a salt thereof;
       (ii) one or more polysaccharides;
       (iii) one or more non-ionic surfactants comprising a poloxamine; and
       (iv) erythritol,
       wherein the aqueous packaging solution has an osmolality of at least about 200 mOsm/kg and a pH of about 6 to about 9;
   (b) packaging the aqueous packaging solution and the ophthalmic device in a manner preventing contamination of the ophthalmic device by microorganisms; and
   (c) sterilizing the packaged solution and the ophthalmic device.

2. The method of claim 1, wherein the tris(hydroxymethyl)aminomethane or a salt thereof is tris(hydroxymethyl)aminomethane hydrochloride.

3. The method of claim 1, wherein the aqueous packaging solution comprises about 0.001 to about 2 wt. %, based on the total weight of the aqueous packaging solution, of the tris(hydroxymethyl)aminomethane or salt thereof.

4. The method of claim 1, wherein the aqueous packaging solution further comprises one or more buffer agents.

5. The method of claim 4, wherein the one or more buffer agents are selected from the group consisting of a phosphate buffer agent, a borate buffer agent, a citrate buffer agent, a (3-(N-morpholino)propanesulfonic acid) buffer agent and mixtures thereof.

6. The method of claim 4, wherein the aqueous packaging solution comprises about 0.001 to about 2 wt. %, based on the total weight of the aqueous packaging solution, of the one or more buffer agents.

7. The method of claim 1, wherein the aqueous packaging solution further comprises one or more of a borate compound, sodium phosphate, and sodium citrate.

8. The method of claim 1, wherein the one or more polysaccharides comprise one or more of hyaluronic acid or a salt thereof, chondroitin sulfate, chitosan, aloe vera, carboxymethylcellulose, hemicellulose, hydroxypropyl methyl cellulose, methylcellulose, and ethylcellulose.

9. The method of claim 1, wherein the aqueous packaging solution further comprises one or more additives selected from the group consisting of an antioxidant, a non-ionic surfactant other than a poloxamine, an osmolyte and mixtures thereof.

10. The method of claim 1, wherein the aqueous packaging solution further comprises one or more additives selected from the group consisting of L-Carnitine, and vitamin E TPGS (tocopheryl polyethylene glycol succinate).

11. A method of preparing a package comprising a storable, sterile ophthalmic device, the method comprising:
   (a) immersing an ophthalmic device in an aqueous packaging solution comprising:
       (i) tris(hydroxymethyl)aminomethane or a salt thereof; and
       (ii) one or more additives selected from the group consisting of a poloxamer di(meth)acrylate, a reverse poloxamer di(meth)acrylate, a poloxamine di(meth)acrylate, and a reverse poloxamine di(meth)acrylate,
       wherein the aqueous packaging solution has an osmolality of at least about 200 mOsm/kg and a pH of about 6 to about 9;
   (b) packaging the aqueous packaging solution and the ophthalmic device in a manner preventing contamination of the ophthalmic device by microorganisms; and
   (c) sterilizing the packaged solution and the ophthalmic device.

12. The method of claim 1, wherein the aqueous packaging solution further comprises one or more additives selected from the group consisting of NaCl, KCl, taurine, glycine, diglycine, alanine; mannitol, sorbitol and propylene glycol.

13. The method of claim 1, wherein the aqueous packaging solution comprises:
   (i) about 0.001 to about 1 wt. %, based on the total weight of the aqueous packaging solution, of the tris(hydroxymethyl)aminomethane or salt thereof;
   (ii) about 0.001 to about 10 wt. %, based on the total weight of the aqueous packaging solution, of the one or more polysaccharides;
   (iii) about 0.001 to about 10 wt. %, based on the total weight of the aqueous packaging solution, of the one or more non-ionic surfactants; and
   (iv) 0.20 to 0.50% W/V of erythritol.

14. The method of claim 1, wherein the ophthalmic device is a contact lens.

15. The method of claim 1, wherein the ophthalmic device is a silicone hydrogel contact lens.

16. The method of claim 1, wherein the aqueous packaging solution does not contain an effective disinfecting amount of a disinfecting agent.

17. The method of claim 1, wherein the aqueous packaging solution does not contain a germicide compound.

18. The method of claim 1, wherein the aqueous packaging solution further comprises one or more additives selected from the group consisting of taurine, carboxymethyl cellulose, hydroxypropylmethyl cellulose, a poly(dimethylacrylamide) polymer having a number average molecular weight of about 10400 to about 65400 and represented by the following structure:

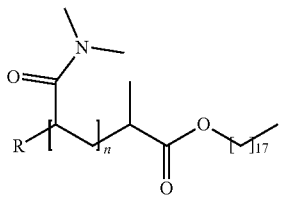

wherein R is CN, OH or H, a polyvinyl pyrrolidone polymer having a number average molecular weight of about 5600 to about 31300 and represented by the following structure:

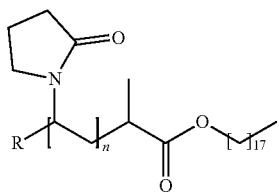

wherein R is CN, OH or H, a poly(acrylic acid)-grafted-poly(ethylene glycol) polymer represented by the following structure:

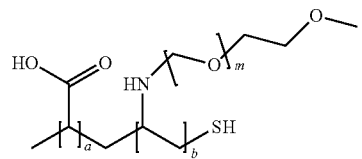

wherein m is 10 to 50, a is 10 to 50 and b is 10 to 50, a poly(acrylic acid)-co-poly(ethylene glycol) monoether acrylate copolymer represented by the structure:

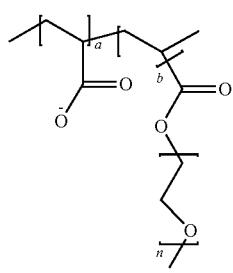

wherein n is 10 to 50, a is 10 to 50 and b is 10 to 50, a poly(dimethylacrylamide)-co-poly(ethylene glycol methacrylate) copolymer represented by the following structure:

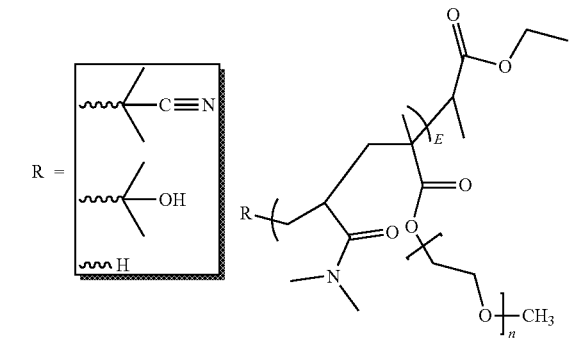

wherein m is 10 to 50, and n is 10 to 50, a poly(acrylic acid)-2-dimethyl ethylenediamine polymer having the structure:

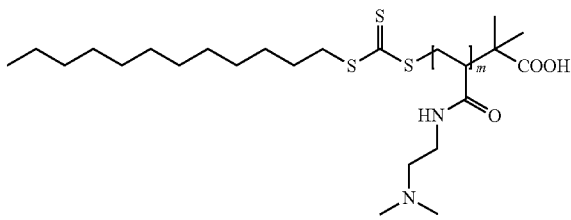

wherein m is 10 to 50, a poly(acrylic acid)-ethylenediamine deprotected polymer having the structure:

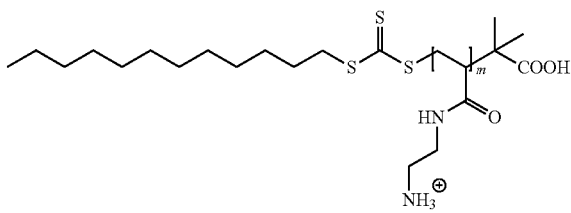

wherein m is 10 to 50, and polyDMA-co-vinyl-4,4-Dimethyl-2-oxazoline-5-one polymer represented by the structure:

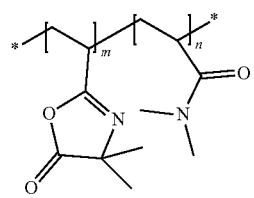

wherein m is 10 to 50 and n is 10 to 50.

19. A method of preparing a package comprising a storable, sterile ophthalmic device, the method comprising:
(a) immersing an ophthalmic device in an aqueous packaging solution comprising:
(i) tris(hydroxymethyl)aminomethane or a salt thereof;
(ii) one or more non-ionic surfactants comprising a poloxamine; and
(iii) erythritol, wherein the aqueous packaging solution has an osmolality of at least about 200 mOsm/kg and a pH of about 6 to about 9;
(b) packaging the aqueous packaging solution and the ophthalmic device in a manner preventing contamination of the ophthalmic device by microorganisms; and
(c) sterilizing the packaged solution and the ophthalmic device.

20. The method of claim 19, wherein the aqueous packaging solution comprises:
   (i) about 0.001 to about 1 wt. %, based on the total weight of the aqueous packaging solution, of the tris(hydroxymethyl)aminomethane or salt thereof;
   (ii) about 0.001 to about 10 wt. %, based on the total weight of the aqueous packaging solution, of the one or more non-ionic surfactants; and
   (iii) 0.20 to 0.50% W/V of erythritol.

\* \* \* \* \*